US00PP18841P3

(12) United States Plant Patent
Korlipara

(10) Patent No.: US PP18,841 P3
(45) Date of Patent: May 27, 2008

(54) *ECHINACEA PURPUREA* PLANT NAMED 'LILLIPUT'

(50) Latin Name: *Echinacea purpurea*
Varietal Denomination: Lilliput

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 118 days.

(21) Appl. No.: 11/389,407

(22) Filed: Mar. 24, 2006

(65) Prior Publication Data

US 2007/0226858 P1 Sep. 27, 2007

(51) Int. Cl.
*A01H 5/00* (2006.01)

(52) U.S. Cl. ..... Plt./428

(58) Field of Classification Search ..... Plt./428, Plt./263
See application file for complete search history.

*Primary Examiner*—Kent L. Bell
*Assistant Examiner*—June Hwu
(74) *Attorney, Agent, or Firm*—Klarquist Sparkman, LLP

(57) ABSTRACT

A new and distinct *Echinacea purpurea* plant named 'Lilliput' characterized by its well branched habit, compact, dwarf habit, numerous medium-small red purple flowers, strong upright stems, and good vigor.

1 Drawing Sheet

Botanical denomination: *Echinacea purpurea.*
Variety designation: 'Lilliput'.

The present invention relates to a new and distinct cultivar of *Echinacea purpurea* and given the cultivar name 'Lilliput'. *Echinacea* is in the family Asteraceae. This new cultivar originated as an open pollinated seedling from a breeding program using *Echinacea* 'Ruby Giant' (an unpatented plant).

This new *Echinacea purpurea* cultivar is distinguished by:

1. Red purple, medium-small flowers.
2. Well branched, compact, dwarf habit.
3. Strong, upright stems.
4. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a close up of the flowers of a two year old *Echinacea purpurea* 'Lilliput' growing in the ground in the field in the summer in Canby, Oreg.

DETAILED PLANT DESCRIPTION

The following is a detailed description of the new *Echinacea purpurea* cultivar based on observations of a one-year-old specimen growing in the ground in full sun under typical outdoor conditions in Canby, Oreg. Canby is in Zone 8 on the USDA Hardiness map. Temperatures range from an average high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—44 cm wide and 31 cm tall to top of flowers.
- *Form.*—Basal clump.
- *Vigor.*—Excellent.
- *Roots.*—Fibrous, with many downward growing and few laterals, ivory in color, Yellow White 158D; roots develop easily from cuttings from the crown or crown divisions.

Stem:
- *Type.*—Ascending.
- *Size.*—30 cm tall to terminal head and 7 mm wide.
- *Internode length.*—1.5 cm to 7 cm.
- *Surface texture.*—Strigose.
- *Color.*—Yellow Green 147C with mottling of Greyed Green 197A.

Leaf:
- *Type.*—Simple.
- *Shape.*—Ovate.
- *Arrangement.*—Alternate.
- *Blade size.*—Basal leaves grow to 20 cm long and 8 cm wide, stem leaves grow to 13 cm long and 7 cm wide.
- *Margins.*—Serrate.
- *Apex.*—Acuminate.
- *Base.*—Attenuate, continuing down petiole.
- *Surface texture.*—Strigose.
- *Venation.*—Pinnate.
- *Color.*—Topside — Deep Green, Between Green 138A and Yellow Green 147A with veins Yellow Green 145C. Bottom — Yellow Green 147B with veins Yellow Green 145C.

*Petiole description.*—Grows to 12 cm if basal leaf, 5.5 cm if cauline leaf and 5 mm wide on both, strigose, Yellow Green 147C overall.

Inflorescence:

*Type.*—Stalked terminal heads.

*Peduncle description.*—Grows to 10.5 cm where leafless, with diameter growing to 6 mm near the flower head, strigose, branched, with one to three flowers per flowering stem; Yellow Green 147C with mottling of Greyed Green 197A.

*Number of flowering stems per plant in summer.*—Ranging from 7 to 12.

*Bloom time.*—Summer until frost in Canby, Oreg.

Flower:

*Type.*—Perfect, zygomorphic.

*Size.*—7 cm wide and 3 cm deep as disc enlarges.

*Form.*—Single row of ray florets held horizontally, cones are flat topped becoming dome shaped with maturity.

*Immature inflorescence.*—2.5 cm wide and 2 cm deep, ray florets held upright and colored Red Purple 59D with greenish tinge, Greyed Yellow 160D. The disc is Red Purple 59A where the bracts are with the very center Yellow Green 144B.

*Ray florets.*—In one series with 23 to 31 ray florets, each oblanceolate, entire, tip two toothed, 3 cm long, 7 mm wide, glabrous on both sides, color on both sides is closest to Red Purple 64C, infertile, no stamen or pistil.

*Disc.*—Flat topped becoming dome shaped with maturity, grow to 5 cm wide and 1.4 cm deep, Orange 28B with Greyed Purple 187A in background.

*Disc florets.*—About 200 in number, 1.2 cm long and 1 mm to 2 mm wide, each floret with one persistent, very stiff bract, 11 mm long, which gives the disc its color, corolla 4 mm long, Yellow Green 144C on bottom ⅔ and Greyed Red 178B on top ⅓; pistil, 1 in number, in disc florets only; ovary 3 mm long, White 155A, style 5 mm long exerted from the corolla, Yellow Green 144C, stigma two-branched Greyed Purple 185A, stamen, 5 in number, in disc florets only, 4 mm long, with the filaments 1.5 mm long and White 155A and the anthers 2.5 mm long and Brown 200A, pollen Yellow Orange 22A.

*Involucral bracts.*—In six leafy series with size largest where closest to the stem, grow to 16 mm long and 3 mm wide, lanceolate, acute, entire, reflexed, strigose, Yellow Green 147B.

*Fragrance.*—Lovely.

*Lastingness.*—Each inflorescence lasts about two weeks.

Seed: Not found.

*Fertility.*—Assumed to be sterile.

Disease and pests: *Echinacea* are susceptible to leaf miners, powdery mildew, bacterial spots, and gray mold. None of these have been observed on plants grown under commercial conditions in Canby, Oreg.

COMPARISONS TO SIMILAR *ECHINACEA*

Compared to *Echinacea purpurea* 'Little Giant', U.S. Plant application Ser. No. 10/872,349, the new variety has smaller, lighter red purple flowers, more flowers, and fewer petal layers. The overall plant habit is lower and wider.

Compared to the parent line using *Echinacea purpurea* 'Ruby Giant' (an unpatented plant), 'Lilliput' has smaller flowers and is a much shorter plant with a much lower and more compact habit.

What is claimed is:

1. A new and distinct *Echinacea purpurea* plant as herein illustrated and described.

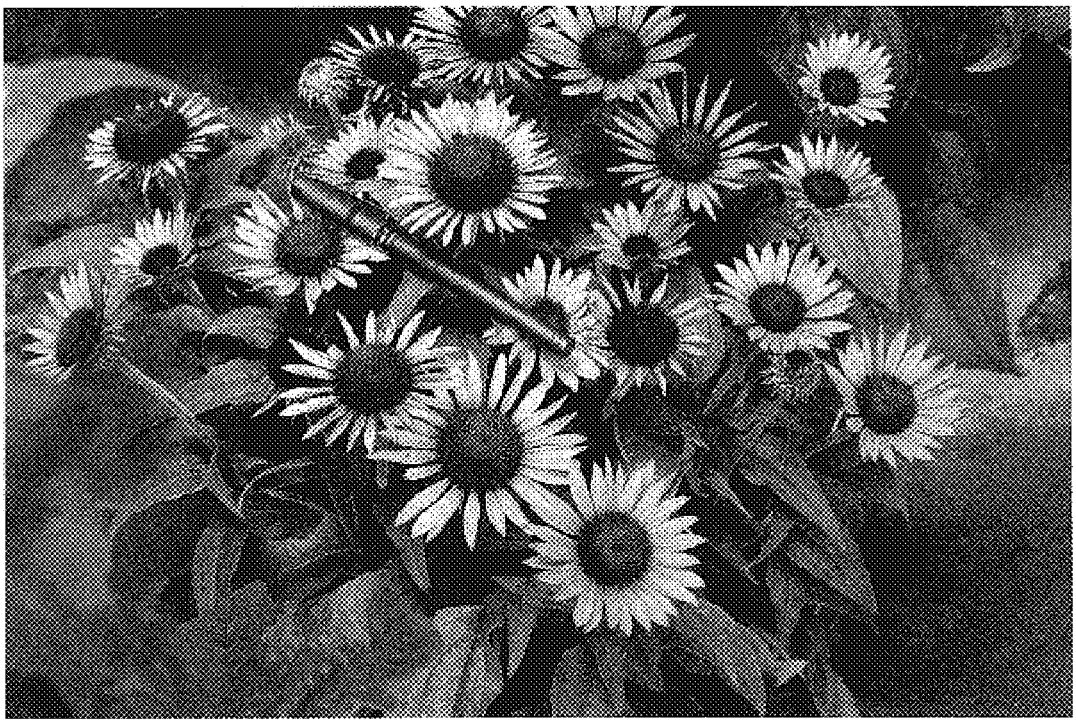

* * * * *